(12) United States Patent
Cranton et al.

(10) Patent No.: US 7,824,331 B1
(45) Date of Patent: Nov. 2, 2010

(54) LARYNGOSCOPE BLADE

(76) Inventors: George D. Cranton, 12033 Gandy Blvd. N. #161, St. Petersburg, FL (US) 33702; Barry L. Wall, One Beach Dr. SE. #2202, St. Petersburg, FL (US) 33701

( * ) Notice: Subject to any disclaimer, the term of this patent is extended or adjusted under 35 U.S.C. 154(b) by 210 days.

(21) Appl. No.: 11/728,321

(22) Filed: Mar. 26, 2007

(51) Int. Cl.
*A61B 1/267* (2006.01)
(52) U.S. Cl. ...................................... 600/190
(58) Field of Classification Search .......... 600/185, 600/190
See application file for complete search history.

(56) References Cited

U.S. PATENT DOCUMENTS

| | | | |
|---|---|---|---|
| 3,426,749 A | 2/1969 | Jephestt et al. | |
| 4,557,256 A | 12/1985 | Bauman | |
| 4,579,108 A | 4/1986 | Bauman | |
| 4,583,527 A | 4/1986 | Musicant et al. | |
| 4,878,486 A | 11/1989 | Slater | |
| 4,958,624 A | 9/1990 | Stone et al. | |
| 5,879,304 A | 3/1999 | Shuchman et al. | |
| 6,623,425 B2 * | 9/2003 | Cartledge et al. | ........... 600/195 |
| 6,666,819 B2 | 12/2003 | Heine et al. | |
| 6,764,443 B1 | 7/2004 | Watson | |
| 6,964,637 B2 | 11/2005 | Dalle et al. | |
| 7,044,910 B2 | 5/2006 | Cartledge et al. | |
| 7,128,710 B1 | 10/2006 | Cranton et al. | |
| 7,153,260 B1 | 12/2006 | Girgis | |

* cited by examiner

*Primary Examiner*—Eduardo C Robert
*Assistant Examiner*—Elana B Fisher
(74) *Attorney, Agent, or Firm*—J. David Haynes

(57) ABSTRACT

A laryngoscope blade is detachably connectable to a hook-on-type laryngoscope handle in conformity with International Standard ISO-7376-1 or ISO 7376-3. The blade comprises a rigid housing having a lower, tongue-engaging flange section extending along the length thereof, a proximal base end provided with hooks or fittings for engaging complementary handle hooks or fittings in compliance with ISO-7376-1 and ISO-7376-3, the proximal base being provided with a hook or flange of such length that the hook or flange comes into contact with the top of the handle such that the blade is prevented from rotating downwardly to such a degree that the distal end of the blade comes into contact with the side of the handle and enabling the blade to be elevated into an operating position to maintain conductivity for powering a light source for the blade.

4 Claims, 4 Drawing Sheets

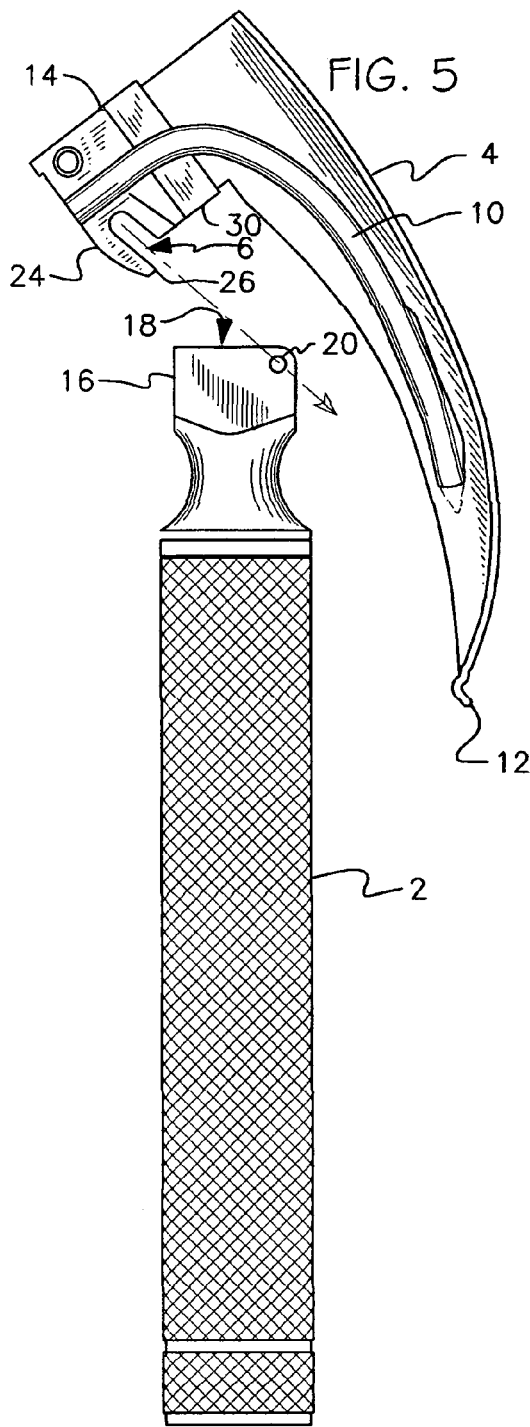
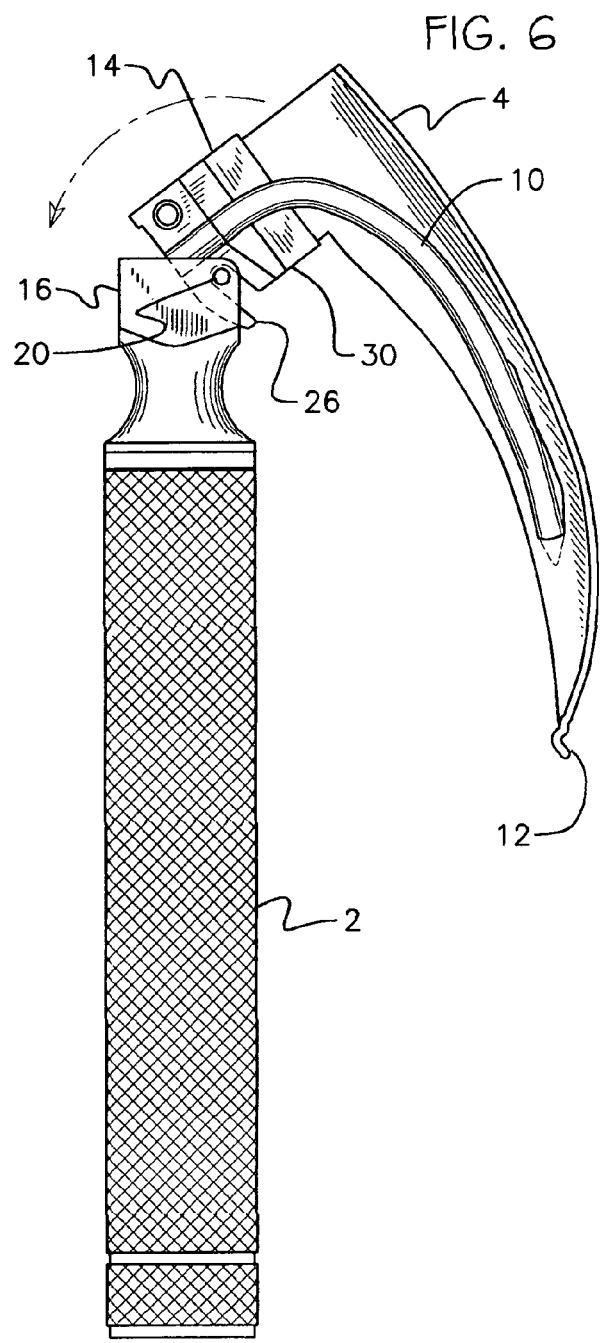

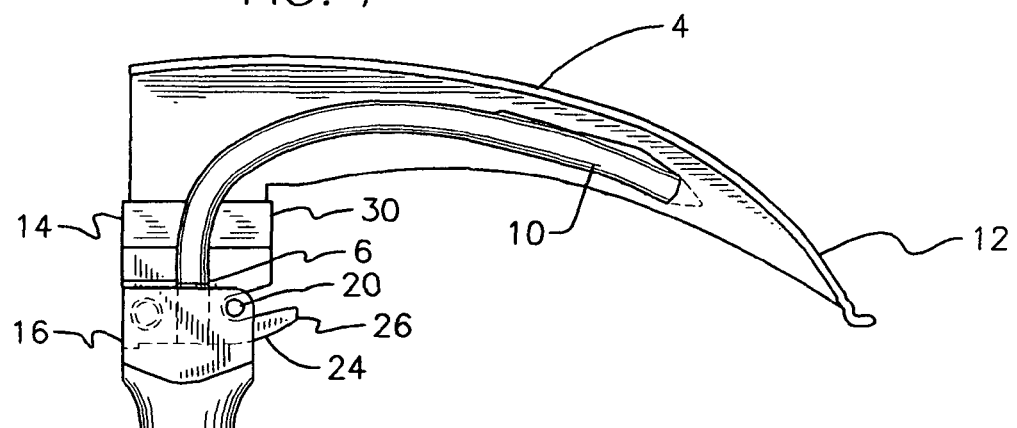
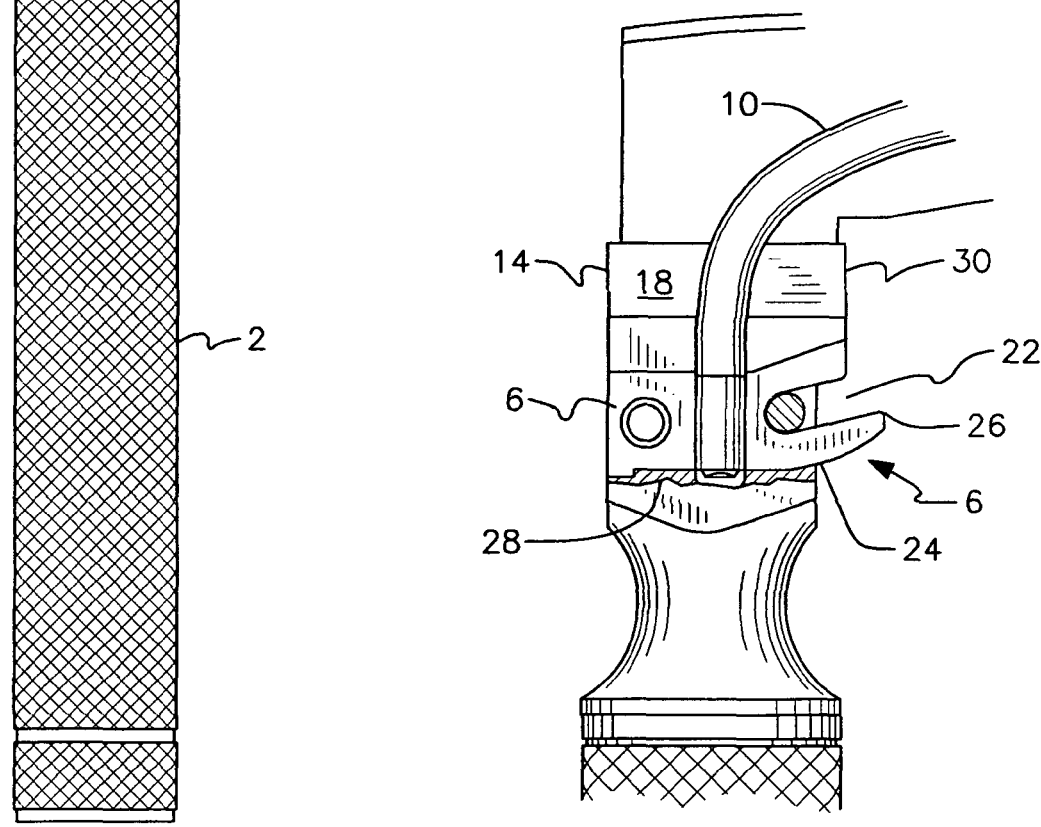

LARYNGOSCOPE BLADE

FIELD OF THE INVENTION

This invention relates to laryngoscopes and particularly to an improved blade for connection to the handle of a laryngoscope to avoid contamination of the handle of the laryngoscope.

DESCRIPTION OF THE PRIOR ART

Laryngoscopes generally comprise a blade and a cooperating handle which are connected together in a generally L-shaped configuration. The handle normally serves as an enclosure for one or more batteries which energize a light source which will illuminate the blade. The means for activating the light source is operated by the blade when it is connected to the handle and placed into the operating or usable position. In fiber optics, the light from the bulb passes through a clear light conductor to the distal end of the blade to illuminate the patient's mouth and larynx during the examination thereof by medical personnel where in a conventional laryngoscope, the lamp in the blade is actuated. The surface on the blade adjacent to the handle is used to press against the tongue and mandible of a patient in a supine position in order to prevent the patient's tongue from obstructing the visual examination of the larynx by medical personnel. Laryngoscope blades are used to examine and visualize a patent's upper airway and aid in the placement of a tracheal tube during intubations, and also during resuscitations. Laryngoscope blades are well known in the industry to present a problem in that the tip of the blade may contaminate the handle when in the folded or flexed position.

While the instrument is useful for examination of the larynx, the primary function of the laryngoscope is to expose the larynx in order to facilitate the insertion of an endotracheal tube. The surface of the laryngoscope blade adjacent the handle is urged against the maxillary and mandible to expose the larynx and trachea in such procedures and the opposite blade surface is positioned opposing the upper and lower front teeth of the patent.

In many of the laryngoscopes in use today, the light source is actuated when the blade is connected to the handle and rotated into the operating position. To turn the light off, the blade must be rotated or folded downwardly toward the handle of the laryngoscope without disengaging the blade from the handle.

In many of the prior art laryngoscopes, the means for connecting the blade to the handle generally comprises a depending appendage at the proximal end of the blade generally in the shape of a heel. The appendage fits into an open channel on the top of the handle and the front end of the heel-shaped appendage hooks under a pivot rod at the front end of the channel. Ball detents are provided in the depending section of the blade which snap into position in the dimples provided in the walls of the channel to thereby fix the position of the blade with respect to the handle. If the ball detents become disengaged from the dimples, then the blade is readily disconnected from the handle or may be rotated to proximately position itself parallel with the hand of the laryngoscope. In this position, the surface of the blade that is inserted into the patients mouth is positioned such that the blade surface contacts the side of the handle of the laryngoscope. This positioning of the blade in contact with the handle of the laryngoscope contaminates the handle with fluids from the patient's mouth.

For the medical personnel, the professional who utilize the laryngoscope, this frequently poses a problem inasmuch as if the device needs to be used again the handle of the laryngoscope must be cleaned. Disposable blades are available which are simply discarded after use; however, the handle of the laryngoscope is reused.

The present invention provides an improved blade for connection to the handle of the laryngoscope which resolves the aforesaid problem in that the contaminated part of the blade does not come in contact with the handle of the laryngoscope when the handle is rotated downwardly to cause the bottom of the heel-shaped appendage to disengage from the light activation means located in the handle of the laryngoscope.

SUMMARY OF THE INVENTION

The present invention is directed to an improved blade for connection to the handle of a laryngoscope which provides for a plurality of blade positions within the general L-shaped configuration and particularly to a connecting systems which allows for the attachment of the blade to the handle in at least one operating position wherein a lighting means is actuated and in at least one ready or folded position in which the lighting means is not activated and the blade may not come into contact with the side of the handle while in this position.

In accordance with the invention, the depending appendage of the blade which interfits with the open channel in the top of the handle is a part shaped like a heel and the front section thereof hooks underneath a hinge pin in the front end of the channel in a conventional fashion. The rear surface of the heel shaped appendage is provided with one or more detents which match the grooves, dimples or other cavities provided in a surface at the rear of the channel. The detents and grooves or dimples provide for at least two blade positions in the L configuration, one is a ready position and one is an operating position or folded position.

When the blade is positioned in the ready position, the front section thereof (heel) which hooks underneath a hinge pin in the handle rotates downwardly toward the top of the laryngoscope handle. In conventional configurations, the front section of the heel does not come in contact with the top of the laryngoscope handle. This enables the blade to assume a position parallel with the laryngoscope handle and to come into contact with the laryngoscope handle.

In recent times, grave concerns have been expressed with regard to the contamination of laryngoscopes, especially with respect to the handle of the laryngoscope and the blade portion which is inserted into patients' throats and often comes into contact with bodily fluids, including blood. Fears have been raised concerning both the possibility of cross-contamination between patients and the infection of medical staff handling the equipment. While disposable laryngoscope blades are useful in effecting sterile laryngoscope blades, the handles upon which the blade is mounted is not disposable and is used repeatedly. If the handle of the laryngoscope is contaminated by the blade coming in physical contact with the handle while in the r ready position, then the risk is great that a sterilized laryngoscope blade may become contaminated even before it is rotated from the ready position to the operating position. This situation, coupled with the present fear of contracting serious diseases such as AIDS, hepatitis, herpes, etc. during surgery or examination, has given rise to a demand for the use of sterilized equipment whenever possible.

In accordance with the invention, the depending appendage of the blade which interfits with the open channel in the top of the handle is a part shaped like a heel and the front section thereof hooks underneath a hinge pin in the front end of the channel of the handle in a conventional fashion. This becomes especially important when it is recognized that current International Standard ISO 7376-1 clearly defines the interrelationship of mechanical fit and electrical contact, thereby permitting interchangeability between handles of the hook-on type and the blades of different manufacturers. International Standard ISO 7376-1 is used with laryngoscope blades that do not use fiber optics. The width of the slot in the handle into which the laryngoscope blade mounts has a width that will accommodate laryngoscope blades having a dimension useful with blades having a light bulb within the blade.

International Standard ISO 7376-3 is for a handle that is intended to be used with a laryngoscope blade that utilizes fiber optics to transmit light to the distal end of the laryngoscope blade. This is usually referred to as a Green System. The heel of a blade for use with an ISO 7376-3 handle has a width that is different from the width of the handle which interfits with an ISO 7376-1 handle. Thus, the user must have the correct blade to interface with the correct handle, either a blade having a light source therein or a blade having a optical network therein for transmitting light from a source that is within the handle.

While the description set forth herein speaks to a blade utilizing fiber optics, the teaching of the heel of the present invention may be utilized with ISO 7376-1 handle or ISO 7376-3 handle.

An object of the present invention is to provide a laryngoscope of design that utilizes blades whose configuration makes it difficult for the blade tip to come in contact with the laryngoscope handle once the blade is fitted onto the laryngoscope handle.

BRIEF DESCRIPTION OF THE DRAWINGS

These and other further objects of the invention will become apparent from the following description of a preferred embodiment of the invention which is shown in the accompanying drawings with like reference numerals indicating corresponding parts throughout and wherein:

FIG. 5 is right side view of the laryngoscope blade of the present invention together with the handle of a laryngoscope before the blade is attached to the handle.

FIG. 6 discloses the laryngoscope blade of the present invention mounted on the handle of a laryngoscope when the handle is in the ready position.

FIG. 7 is a right side view of the laryngoscope blade of the present invention together with the handle of the laryngoscope with the laryngoscope blade attached to the handle.

FIG. 8 is a partial cross-sectional view of the heel of the laryngoscope blade shown in FIG. 7.

Figure 1:
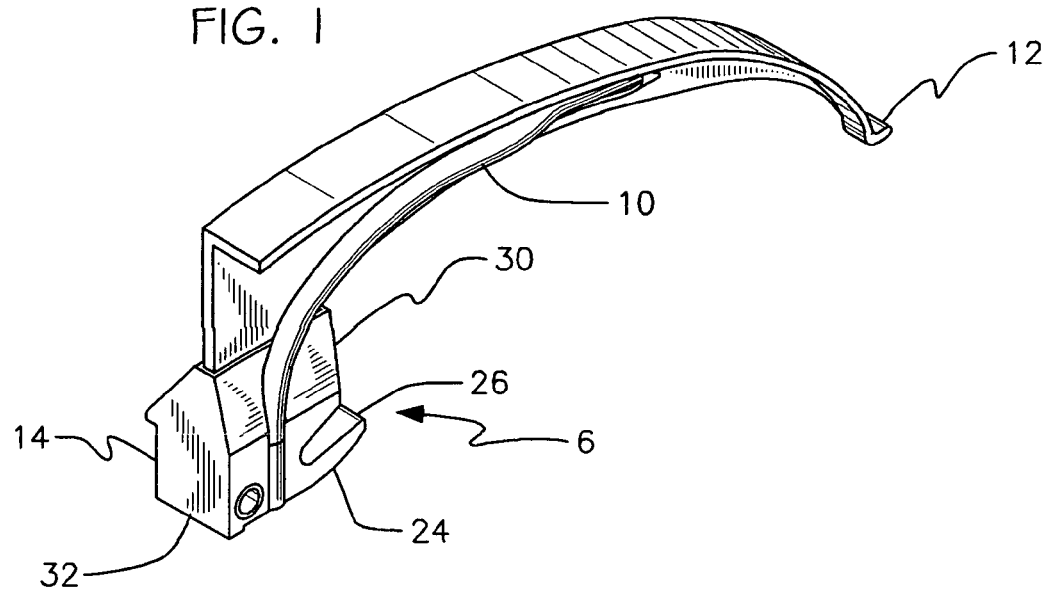
FIG. 1 is a perspective view of a laryngoscope blade disclosing a preferred embodiment of the present invention.

LIST OF REFERENCE NUMERALS UTILIZED IN THE DRAWING 2 handle of laryngoscope
4 laryngoscope blade
6 claw-type fitting
8 longitudinal right angle channel
10 tube of optical fibers
12 distal end of blade
14 heel or heel-shaped depending appendage attached to laryngoscope blade
16 mounting end of handle when laryngoscope blade attaches
18 Slot in mounting end of laryngoscope handle where blade attaches
20 hinge pin in slot 18 for receiving heel 14
22 inclined slot in heel 14
24 tongue or depending appendage in heel
26 end of tongue
28 bottom of slot 18
30 right end of heel 14
32 left end of heel 14

DETAILED DESCRIPTION OF THE PREFERRED EMBODIMENT

Referring now to the drawings wherein like numerals are used to reference the same components therein FIG. 7, discloses a laryngoscope blade 4 according to the present invention as used with handle 2 of a laryngoscope. Blade 4 extends substantially at right angles to handle 2. Blade 4 is detachably secured to handle 2 by claw-type fitting 6 and is formed to define a longitudinal right-angled channel 8 to enable a practitioner to see along the length of the blade and thus into a patient's larynx and also to provide a passage for intubation. Blade 4 carries tube 10 of optical fibers in the longitudinal right angle channel 8 for transmitting light from laryngoscope handle 2 toward distal end 12 of blade 4.

It should be clearly understood that the particular form of laryngoscope blade illustrated in the drawings is only one example of a considerable number of different shaped blades which are commonly available for use in various different circumstances, and that the present invention extends to the provision of all forms of laryngoscope blades and not only to that which is illustrated. Some blades have the light source within the blade while other blades utilize a fiber optics system within the blade from a light source located within the handle of the laryngoscope.

It should be clearly understood that the particular form of the configuration of heel-shaped depending appendage 14 of the blade, also referred to as the foot of the blade 4 and the manner of manufacture of heel 14 may be as disclosed in U.S. Pat. No. 7,128,710 B1 or other configurations.

Mounting end 16 of handle 2 has a slot 18 formed therein transversed by a hinge pin 20 and a pair of laterally spaced and opposed detents (not shown), one on each lateral side of slot 18. Heel 14 matingly mounts onto mounting end 16 of handle 2 as disclosed in FIG. 5 and FIG. 6.

Referring to FIG. 8, heel-shaped depending appendage 14 has an inclined slot 22 formed laterally across the right end thereof, which slot receives the hinge pin 20 of handle 2 when assembled on handle 2. Inclined slot 22 is disposed in heel 14 at its distal end, that is, the portion of heel 14 which is most removed from the back (proximal end) of the blade 4. The lower portion of heel 14 comprises a tongue or appendage 24 which protrudes from heel 14 a substantial distance past surface 30 of heel 14. Referring to FIG. 8, when blade 4 is caused to rotate around hinge pin 20, the distal end 26 of tongue 24 comes into obstructive contact with bottom 28 of slot 18 in the top of handle 2 to thus inhibit further rotation of blade 4 around hinge pin 20 as disclosed in FIG. 6. The length of tongue 24 past right end 30 of heel 14 is a function of the physical dimensions of slot 18 and the depth of slot 18 and the distance from hinge pin 20 to bottom 28 of slot 18. The length of tongue 26 must be of such length that end of tongue 26 is engages bottom 28 of slot 18 to determine the rotation of blade 4 about hinge pin 20. Thus, the distal end 12 of blade 4 is prevented from coming in contact with the side of handle 2. Otherwise, blade 4 functions to attach to handle 2 as disclosed in FIG. 5 and FIG. 6 as do blades disclosed in the prior art. The present invention relates to the physical dimensioning of heel 14 and, in particular, tongue or appendage 24.

Figure 3:
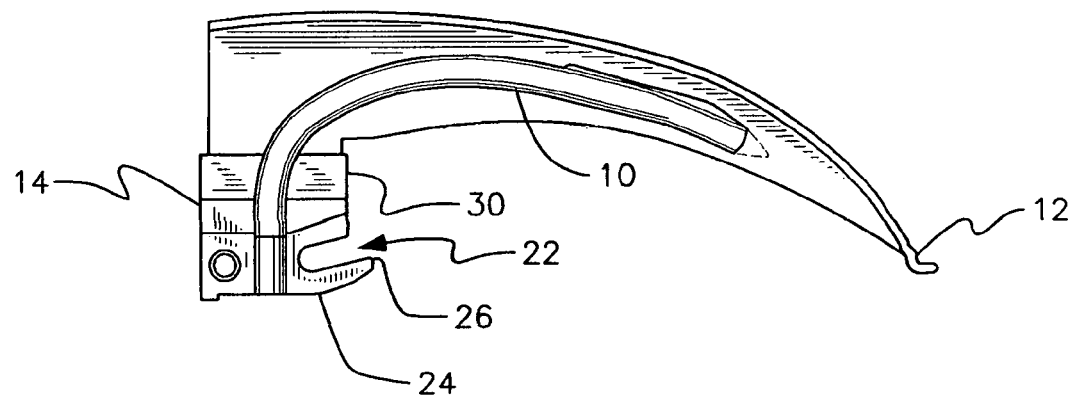
FIG. 3 is a right side view of the laryngoscope blade with the heel of the present invention.
Figure 4:
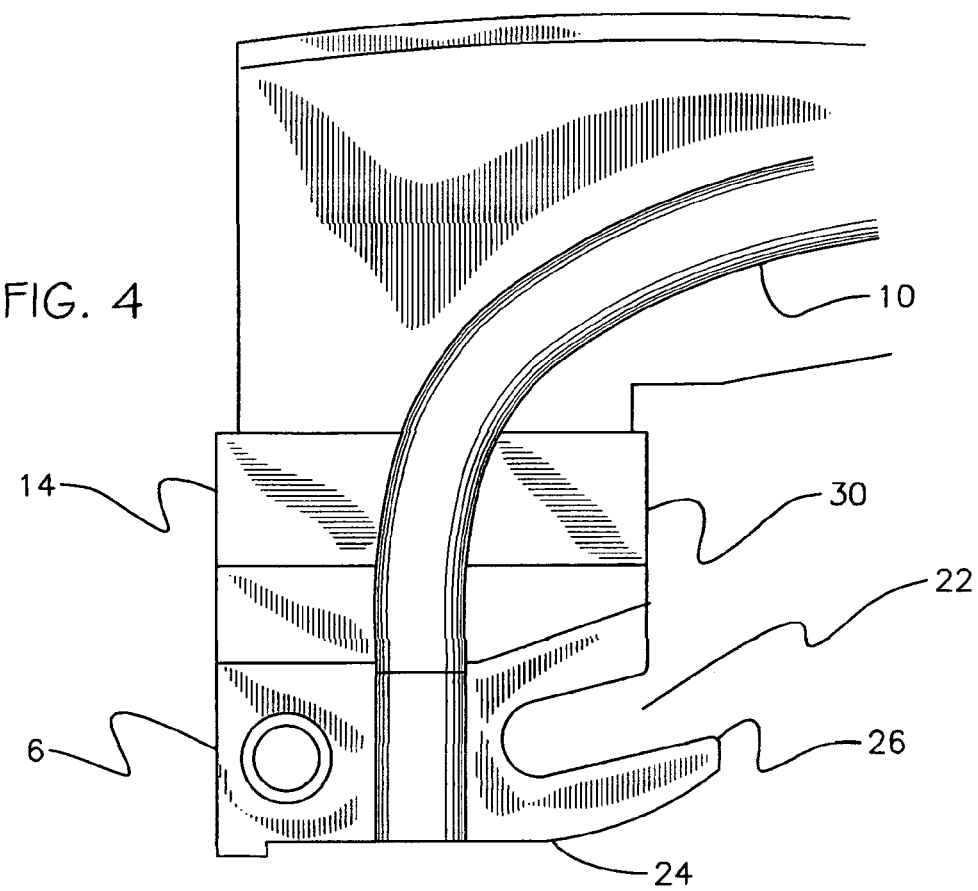
FIG. 4 an enlarged right side view of the heel of the present invention.

Referring to FIG. 3 and FIG. 4, it may be appreciated that tongue 24 of inclined slot 22 protrudes farther from heel 14 than surface 30 which is referred to as the right end of heel 14 as distinguished from surface 32 (FIG. 1) which is referred to as the left end of heel 14. In prior art devices the end 30 of heel 14 and distal end 26 of tongue 24 lie in the same vertical plane. It may be appreciated by reference to FIG. 6 that the plane within which surface 30 of heel 14 lies and end of tongue 26 are not the same. End 26 of tongue 24 is of such a length that it comes into contact with handle 2 as blade 4 is rotated about hinge pin 20 within slot 18 in handle 2. In a preferred embodiment, end of tongue 26 extends approximately 3 mm longer than similar tongues in the prior art. This means that the length of tongue 26 would be approximately 3 mm past the plane wherein lies right end 30 of heel 14.

Figure 2:
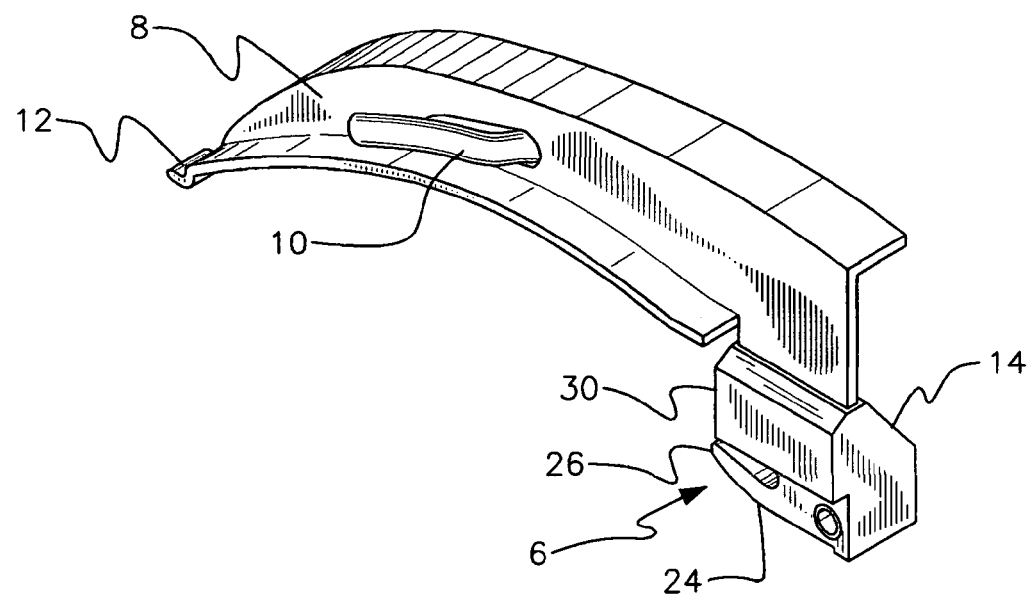
FIG. 2 is a side-rear elevational view of the laryngoscope blade disclosing the heel portion

FIG. 1 and FIG. 2 disclose perspective views of blade 4 and heel-shaped depending appendage 14 also referred to as heel 14 of blade 4.

This extension of tongue 26 prevents the movement of blade 4 as disclosed in FIG. 6 to such a degree that handle 4 may not come in contact with handle 2. In prior art configurations, blade 4 may rotate downwardly toward handle 2 until blade 4 actually comes into contact with handle 2. Any contaminant on handle 2 may then be transferred to blade 4. It should be appreciated that it is not the practice of users of laryngoscopes to sterilize handle 2 in an autoclave or other high temperature device in that handle 2 includes a light source (not shown) and batteries (not shown) inside handle 2 as is well known in the prior art.

Referring now to FIG. 5 and FIG. 6, one may appreciate that blade 4 is pivotally mounted to handle 2. Claw-type fitting 6 engages hinge pin 20. Thus, blade 4 may be rotated into an operating position where blade 4 is perpendicular to handle 2. In this position, in a conventional laryngoscope combination, the light source, whether in handle 2 or on blade 4, is energized to permit visual inspection of the larynx or esophagus of the patient. Blade 4 may also be rotated into what is normally referred to as a ready position as is disclosed in FIG. 6. In this position the lighting means (not shown) is not energized. In a conventional configuration of a laryngoscope the distal end 12 of blade 4 may touch the side of handle 2.

In a preferred embodiment of the present invention, it may be observed that blade 4 and handle 2 are at an angle of approximately 15 degrees more or less when handle 2 is in the ready position. The angulation is not critical other than to make sure that blade 4 and handle 2 do not contact each other. This avoids contamination that may be on handle 2 from being transferred to blade 4 when distal end 12 of blade 4 would contact handle 2. In actual use, the user grasps handle 2 before, during and after use of the laryngoscope. If the user's hand becomes contaminated, then it is advisable to regulate the angular dependeture of blade 4 such that blade 4 will not come in contact with the hand of the user of the laryngoscope. An ideal angular placement of blade 4 when blade 4 is in the ready position may be 30 degrees with regard to handle 2.

The particular angle of dependeture of blade 4 to handle 2 is a function of the length of tongue 30 as tongue 30 comes into obstructive contact with slot 18 in the mounting end 16 of handle 2. The longer the tongue 24, the more restricted will be the pivoting or rotation of handle 4 around cross pin 20 in slot 18.

While only a single embodiment of this invention has been shown and described, it is apparent that changes can be made therein without departing from the scope of this invention as claimed in the following claims.

We claim:

1. In an examining device comprising:

a blade having a proximal end and a distal end, a handle having a bottom, a side, a top, an open slot on said top, said slot having a front end, a rear end, a left side, a right side and a bottom, and a hinge pin transverse said front end of said open slot, and means to detachably secure said blade to said handle in an L-shaped configuration comprising:

an improved heel-shaped depending appendage disposed on said proximal end of said blade, said heel shaped depending appendage having a right end and a left end, said right end of said heel-shaped depending appendage adapted to hook under said hinge pin in said front end of said open slot provided in said top of said handle, said slot being adapted to matingly receive said heel-shaped depending appendage on said blade, said improvement comprising:

means to detachably and rotatably secure said blade to said handle in at least two positions in said L-shaped configuration, one position being an operating position and one position being a folded position, wherein said means to secure said blade to said handle comprises a claw-type fitting having a left end and a right end, said right end of said claw-type fitting having an inclined slot disposed in said right end of said heel-shaped depending appendage and laterally across said right end of said heel-shaped depending appendage thereof which wherein said slot receives there into said hinge pin of said handle for rotating, mating engagement of said blade and said handle thereof;

said inclined slot having a lower tongue-shaped protrusion having an end which extends past said right end of said heel-shaped depending appendage a sufficient distance such that when said blade is rotated to said folded position, said end of said tongue-shaped protrusion abuts said bottom of said open slot provided in said top of said handle to inhibit rotation of said blade whereby said distal end of said blade does not contact said side of said handle.

2. A heel-shaped appendage for use in attaching a laryngoscope blade to a handle of a laryngoscope said handle having a bottom, a side, a top, an open slot on said top, said slot having a front end, a rear end, a left side, a right side and a bottom, and a hinge pin transverse said front end of said open slot, said heel-shaped appendage comprises:

a first side;

a second side; and an inclined slot disposed in said second side of said heel-shaped appendage and laterally across said second side of said heel-shaped appendage;

wherein said inclined slot has a bottom portion that extends past said second side of said heel-shaped appendage.

3. A heel-shaped appendage as set forth in claim 2 wherein said bottom portion of said slot that extends past said second side of said heel-shaped appendage engages an open slot provided in the top of the laryngoscope handle when said blade is rotated downwardly toward the handle of said laryngoscope to prevent said blade from coming in contact with said handle.

4. A heel-shaped appendage as set forth in claim 2 wherein said bottom portion prevents said blade from contacting the side of the laryngoscope handle when said heel-shaped appendage is attached to the proximal end of a laryngoscope blade and rotatably attached on a laryngoscope handle.

* * * * *